(12) United States Patent
Laghi

(10) Patent No.: US 6,764,631 B1
(45) Date of Patent: Jul. 20, 2004

(54) METHOD FOR MAKING A THERMOFORMABLE LINER

(76) Inventor: Aldo A. Laghi, 14410 Eagle Point Dr., Clearwater, FL (US) 33762

(*) Notice: Subject to any disclaimer, the term of this patent is extended or adjusted under 35 U.S.C. 154(b) by 273 days.

(21) Appl. No.: 10/063,809

(22) Filed: May 15, 2002

Related U.S. Application Data

(63) Continuation-in-part of application No. 09/681,694, filed on May 22, 2001, now abandoned.

(51) Int. Cl.[7] .......................... B29C 33/40; B29C 51/00
(52) U.S. Cl. ...................... 264/222; 264/220; 264/223; 264/227; 264/342 R
(58) Field of Search ................ 264/220, 222, 264/223, 227, 342 R

(56) References Cited

U.S. PATENT DOCUMENTS

| | | | | | |
|---|---|---|---|---|---|
| 1,907,511 A | * | 5/1933 | Davies | ................ | 623/33 |
| 3,377,416 A | * | 4/1968 | Kandel | ................ | 264/222 |
| 4,696,780 A | * | 9/1987 | Hagglund | ................ | 264/222 |
| 5,364,580 A | * | 11/1994 | Prent | ................ | 264/138 |
| 5,888,231 A | * | 3/1999 | Sandvig et al. | ................ | 623/36 |
| 5,980,576 A | * | 11/1999 | Graf et al. | ................ | 623/33 |
| 5,980,803 A | * | 11/1999 | Slemker et al. | ................ | 264/222 |
| 6,334,854 B1 | * | 1/2002 | Davis | ................ | 602/6 |
| 6,485,776 B2 | * | 11/2002 | Janusson et al. | ................ | 427/2.31 |
| 6,626,952 B2 | * | 9/2003 | Janusson et al. | ................ | 623/36 |

* cited by examiner

Primary Examiner—Allan R. Kuhns
(74) Attorney, Agent, or Firm—Ronald E. Smith; Smith & Hopen, P.A.

(57) ABSTRACT

A custom-fitting prosthetics liner is made without mixing silicone and without making a mold. A thermoformable liner is made by preparing a negative cast from a patient's residual limb, preparing a positive cast from the negative cast, and placing a thermoformable tubular liner over the positive cast. The positive cast and liner are heated in an oven for a predetermined time and temperature. Having acquired a new geometry, the cast and liner are removed from the oven and allowed to cool to room temperature. The liner is then removed from the cast. Alternatively the liner is heated, placed over the positive cast, cooled and removed. The interior surface of the liner conforms to the shape of the cast. The liner is elastic so that it returns to its new geometry when stretched and released. It therefore holds on to a residual limb even when the residual limb shrinks.

24 Claims, 2 Drawing Sheets

METHOD FOR MAKING A THERMOFORMABLE LINER

CROSS-REFERENCE TO RELATED DISCLOSURES

This disclosure is a continuation-in-part of an earlier disclosure filed by the same inventor on May 22, 2001, Ser. No. 09/681,69, entitled: "Method of Making A Thermoformable Liner," now abandoned.

BACKGROUND OF THE INVENTION

1. Field of the Invention

This invention relates, generally, to the art of prosthetics. More particularly, it relates to a method for making a hard socket or a liner by thermoforming.

2. Description of the Prior Art

Some amputees wear socks on their residual limb to provide cushioning between the residual limb and the surface of a hard socket. However, socks cannot provide an airtight seal between the residual limb and the socket. As a result, various means are employed to prevent relative motion between the residual limb and the socket, but such means are largely inadequate.

Accordingly, inventors in the prosthetics industry have developed various rubber-like cushioning means that are adapted to be worn like socks over the residual limb.

Such cushioning means provide an airtight seal around the residual limb. This enables creation of a vacuum in the unoccupied part of the hard socket, i.e., in the lowermost end of the socket below the residual limb. The vacuum substantially prevents relative movement between the residual limb and the socket.

Most rubber-like liners are unacceptable, however, because they are skin-unfriendly and have other unwanted side effects. Urethane, for example, provides the desired cushioning effect but can irritate the skin and create odors.

Silicone RTV has become the material of choice for custom liners. A mold is made that duplicates the geometry of the patient's stump and liquid RTV silicone is poured into the mold. The mold is opened after twenty four hours and the custom silicone liner is retrieved.

There are several drawbacks to this process. First, it requires the mixing of silicone. Second, it requires the making of a mold. Moreover, the process takes more than a day to complete.

However, in view of the prior art considered as a whole at the time the present invention was made, it was not obvious to those of ordinary skill in the art how a custom liner could be made in the absence of silicone mixing, mold-making, and the like.

SUMMARY OF THE INVENTION

The longstanding but heretofore unfulfilled need for an improved method for making custom liners is now met by a new, useful, and nonobvious invention. The heart of the invention is its provision of a thermoformable prosthetic liner. The novel method of making a thermoformable tubular liner for use in a prosthetic appliance includes the steps of preparing a negative cast from a patient's residual limb, preparing a positive cast from the negative cast, and placing a thermoformable tubular liner over the positive cast.

The positive cast and the thermoformable tubular liner are then heated in an oven for a predetermined amount of time, such as thirty minutes, at a predetermined temperature such as about ninety to one hundred degrees Celsius. The cast and thermoformable tubular liner are removed from the oven and allowed to cool to room temperature. The thermoformable tubular liner is then removed from the cast. An interior surface of the thermoformable tubular liner will now be observed to conform to the shape of the positive cast.

A procedure that produces the most consistent results includes the steps of preheating the positive cast, placing the thermoformable liner over the heated cast, placing both the positive cast and the thermoformable liner in the oven, and removing both items from the oven and letting them cool to room temperature.

A faster procedure includes the steps of preheating the thermoformable liner, placing the thermoformable liner over the positive cast, and letting both items cool to room temperature.

The thermoformable tubular liner exhibits elasticity when cooled to room temperature. Accordingly, it returns to its pre-stretched size and shape when stretched and released at room temperature.

The thermoformable tubular liner is adapted to be stretched and fitted over a residual limb. Due to its elasticity, it remains on the residual limb even as the residual limb shrinks during the day.

The positive cast may also be preheated in the oven for a predetermined amount of time such as two to three hours at a predetermined temperature such as about ninety to one hundred degrees Celsius prior to said step of placing the thermoformable tubular liner over the positive cast.

The thermoformable tubular is formulated by mixing triblock copolymers of the styrene, ethylene styrene type with mineral oils at a predetermined concentration. The predetermined concentration is about 200 to 400 parts of mineral oil per 100 parts of polymer.

A fabric may also be applied in overlying relation to an exterior surface of the liner. When a fabric is applied, the step of applying the fabric is performed after the step of placing the thermoformable tubular liner over the positive cast and prior to the step of heating the positive cast and thermoformable tubular liner in the oven.

A general object of the invention is to provide a method for making a custom prosthetic liner by a thermoforming process.

A more specific object is to provide a method for making a custom prosthetic liner where the method requires no silicone mixing and no mold-making.

Another very important object is to provide a thermoformable liner that acquires a new geometry upon being heating in an oven and cooled to room temperature, and which returns to that new geometry upon being stretched and released at room temperature so that it may be worn on a residual limb all day without becoming loose if the residual limb shrinks during the day.

It is also an object of this invention to provide a method for making a thermoformable liner that is easy and economical to follow and that results in high quality liners.

Another object is to provide a thermoformable liner having elasticity so that it may be turned inside out to facilitate putting it on and taking it off.

Yet another object is to provide a thermoformable liner exhibiting elasticity so that it can be used with residual limbs having irregular geometries.

These and other important objects, advantages, and features of the invention will become clear as this description proceeds.

BRIEF DESCRIPTION OF DRAWINGS

For a fuller understanding of the nature and objects of the invention, reference should be made to the following detailed description, taken in connection with the accompanying drawings, in which.

DETAILED DESCRIPTION

Figure 1:
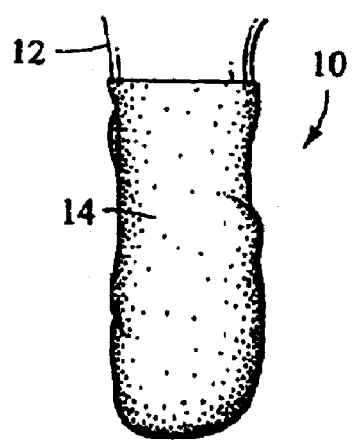
FIG. 1 is a front elevational view of a residual limb covered with plaster.
Figure 2:
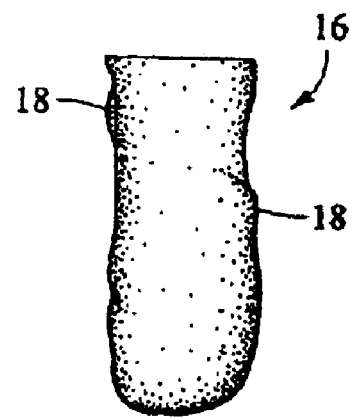
FIG. 2 is a front elevational view of a positive cast made from a negative cast.

Referring to FIG. 1, it will there be seen that the reference numeral 10 denotes the first step in the novel method. A patient's residual limb 12 is covered with plaster 14 in a well-known way to create a negative plaster cast of said residual limb. FIG. 2 depicts the positive plaster cast 16 that is made from the negative. Prominences 18 in said positive plaster cast 16 correspond to bony prominences in the patient's residual stump. One or more of the prominences 18 are reduced in size as deemed appropriate by the prosthetist. Other cast modifications may be required as well. See pages 105–111 of an article entitled "Clinical Aspects of Lower Extremity Prosthetics," published by the Canadian Association of Prosthetists and Orthosists, ISBN No. 0-921832-02-8. For above-knee amputations, different considerations apply to the modification of the cast, but the process is similar.

Figure 3:
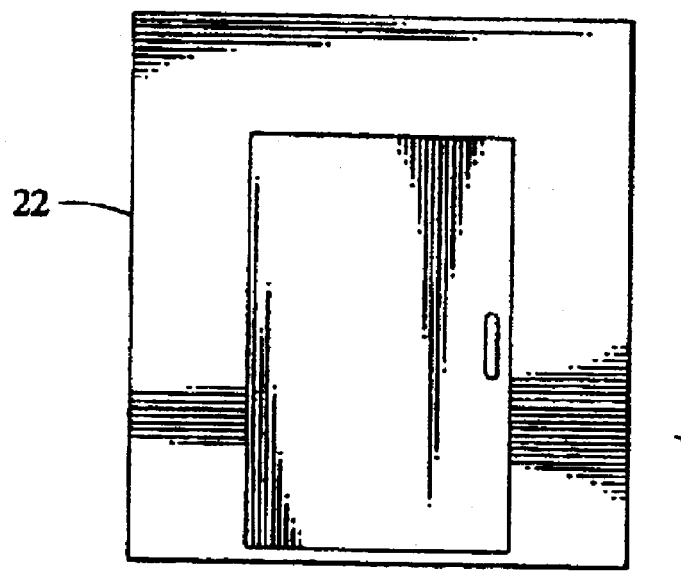
FIG. 3 is a perspective view depicting the placing of the positive cast in an oven.
Figure 3:
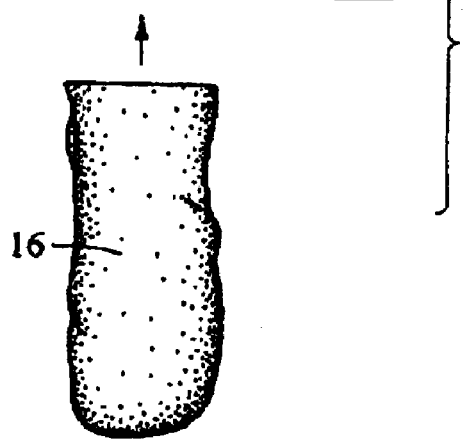

Positive cast 16 is then preheated for about two to three hours in oven 22 (FIG. 3) to a low temperature such as 90° C. to 100° C.

Figure 4:
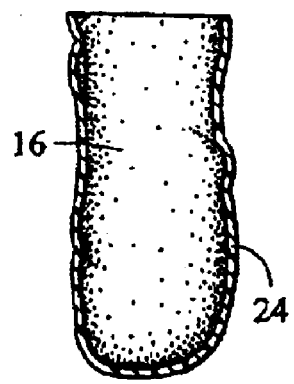
FIG. 4 depicts the placing of a thermoformable liner on the positive cast after said positive cast has been removed from said oven.

Cast 16 is removed from oven 22 and liner 24 is stretched thereonto as illustrated in FIG. 4. Liner 24 has a conventional, tubular configuration before it is stretched onto cast 16.

Figure 5:
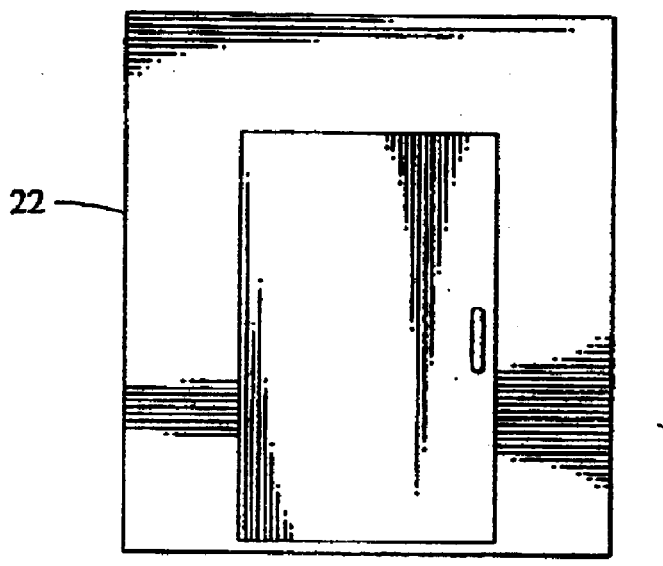
FIG. 5 depicts the placing of the liner and positive cast back into said oven.
Figure 5:
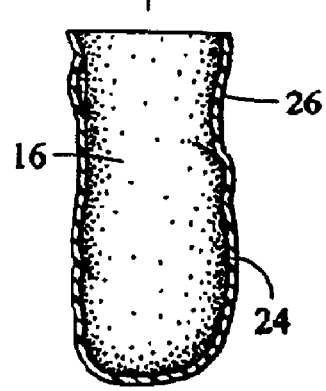

FIG. 5 depicts the placing of cast 16 having liner 24 thereon into oven 22. The cast and liner are left in the oven for about thirty minutes or until the liner becomes pliable. Liner 24, being formed of a suitable thermoformable material, becomes molded to the shape of positive cast 16 in this step of the method, i.e., it acquires a new geometry. Positive cast 16 and liner 24 are removed from oven 22 upon expiration of said thirty minute time period and allowed to cool to room temperature. Liner 24 is then removed from positive cast 16.

Figure 6:
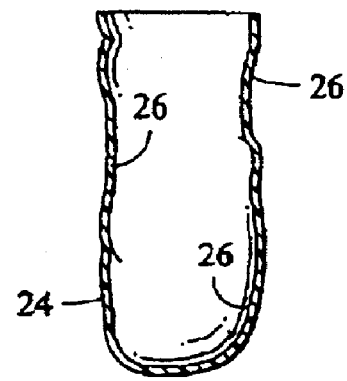
FIG. 6 depicts the novel liner after it has been removed from the positive cast.

FIG. 6 depicts said liner 24 after its separation from said positive cast 16. Note that the liner is no longer tubular in configuration; it has been thermoformed so that its interior surface matches the shape of positive cast 16. Accordingly, there are concavities such as concavity 26 formed in said interior surface, said concavities matching bony prominences 18 of positive cast 16. Significantly, the formation of these concavities is permanent, i.e., they will not disappear as the patient uses the liner.

Although the steps of the novel method may be deemed to be complete at this point, if the prosthetist want to make a hard socket at this time, liner 24 is left on positive cast 16 and the hard socket is laminated directly over said liner. Upon completion of the lamination, positive cast 16 is then separated from liner 24 and the hard socket.

A faster procedure omits the step of preheating the positive cast in the oven, instead, the thermoformable liner is preheated until it becomes pliable, the heated thermoformable liner is placed over the positive cast, and both the thermoformable liner and positive cast are allowed to cool to room temperature. The thermoformable liner is then removed from the positive cast and is ready for use. Its interior surface matches the exterior surface of the positive cast. Moreover, the thermoformable liner made with this fast procedure acquires a new geometry where it conforms to the positive cast, and it returns to its new geometry when stretched and released, Just as when made with the lengthier procedure. The lengthier procedure (preheating the positive cast, placing the thermoformable liner over the heated positive cast, placing both items in the oven, and letting them cool) is considered to be the safer procedure and produces the most consistent results.

Most thermoplastic rubbers such as thermoplastic urethanes, ethylene/propylene TPR'", and Santoprene® rubber, manufactured by Monsanto, are thermoformable. However, these rubbers are generally too hard or skin-unfriendly to be used for liners.

Suitable formulations include mixtures of triblock copolymers of the styrene, ethylene styrene type mixed with mineral oils in the concentration of 200 to 400 parts of oil per 100 parts of polymer. Formulations of this type produce elastomers having a durometer reading of 40–60 on the "00" scale.

Significantly, after liner 24 has been removed from oven 22, it retains its elastomeric quality. Because it is formed of a thermoformable material, it will not return to its pre-heated size and shape after it has cooled. However, when it is stretched and released at room temperature, it returns to the size and shape it had upon being removed from the oven and cooled.

More particularly, liner 24, being formed of the disclosed thermoformable material, maintains the new geometry it acquires as a result of the novel process. Moreover, it exhibits elasticity in that when stretched and released at room temperature, it returns to said newly acquired geometry. No re-heating is required for the material to exhibit such elasticity. Thus, it may be worn on a residual limb throughout the day because its elasticity holds it to said residual limb as said residual limb shrinks. Most amputees experience a shrinking of the limb as the day goes on. A residual limb will shrink about 2–5% where a liner without a pin is used and will shrink about 5–10% when a liner having a pin is used. The greater shrinkage associated with a liner having a pin is due to the milking action of that type of liner. Residual limbs having fluid build-up or circulatory problems may shrink more than others. However, the elasticity of the novel liner is sufficient to accommodate residual limbs of widely varying sizes and shapes and to hold to said residual limbs throughout the day.

The elasticity of the novel liner also enables it to fit residual limbs having irregular geometries. Moreover, its elasticity enables it to be turned inside out, thereby making it easy to put on and take off.

Liner 24 may also be covered by a fabric 26. The temperature in the oven is insufficient to ignite said fabric. Fabric 26 provides a thin, non-stick barrier between the gel-like base of the liner and the hard socket Moreover, it prevents liner 24 from stretching to an unacceptable degree. Fabric 26 imparts tear strength to the liner and facilitates the introduction of the stump into the hard socket. Moreover, for liners having a distal attachment system, the fabric imparts low longitudinal stretch to the liner to prevent pistoning.

A liner not covered with fabric is also within the scope of this invention. Such a liner would not be as durable as a fabric-covered liner nor would it function as well.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,
What is claimed is:

1. A method of making a thermoformable tubular liner for use in a prosthetic appliance, comprising the steps of:
   preparing a negative cast from a patient's residual limb;
   preparing a positive cast from said negative cast;
   placing a thermoformable tubular liner over said positive cast;
   heating said positive cast and thermoformable tubular liner in an oven for a predetermined amount of time at a predetermined temperature so that said thermoformable tubular liner acquires a new geometry;
   removing said cast and thermoformable tubular liner from said oven and allowing said cast and thermoformable tubular liner to cool to room temperature;
   removing said thermoformable tubular liner from said cast;
   an interior surface of said thermoformable tubular liner conforming to the shape of said positive cast;
   said thermoformable tubular liner exhibiting elasticity when cooled to room temperature and returning to its new geometry when stretched and released at room temperature;
   said thermoformable tubular liner adapted to be stretched and fitted over a residual limb;
   whereby said thermoformable tubular liner remains on said residual limb even as said residual limb shrinks during the day.

2. The method of claim 1, wherein said predetermined amount of time is about thirty minutes.

3. The method of claim 2, wherein said predetermined temperature is about ninety to one hundred degrees Celsius.

4. The method of claim 1, further comprising the step of preheating said positive cast in said oven for a predetermined amount of time at a predetermined temperature prior to said step of placing said thermoformable tubular liner over said positive cast.

5. The method of claim 4 wherein said predetermined amount of time of said preheating step is about two to three hours.

6. The method of claim 4, wherein said predetermined temperature of said preheating step is about ninety to one hundred degrees Celsius.

7. The method of claim 1, further comprising the step of formulating said thermoformable tubular liner by mixing triblock copolymers of the styrene, ethylene styrene type with mineral oils at a predetermined concentration.

8. The method of claim 7, wherein said predetermined concentration is about 200 to 400 parts of mineral oil per 100 parts of polymer.

9. The method of claim 1, further comprising the step of applying a fabric in overlying relation to an exterior surface of said liner.

10. The method of claim 9, wherein the step of applying the fabric is performed after the step of placing the thermoformable tubular liner over the positive cast and prior to the step of heating the positive cast and thermoformable tubular liner in the oven.

11. A method of making a thermoformable tubular liner for use in a prosthetic appliance, comprising the steps of:
   preparing a negative cast from a patient's residual limb;
   preparing a positive cast from said negative cast;
   placing a thermoformable tubular liner over said positive cast;
   formulating said thermoformable tubular liner by mixing triblock copolymers of the styrene, ethylene styrene type with mineral oils at a predetermined concentration;
   heating said positive cast and thermoformable tubular liner in an oven for a predetermined amount of time at a predetermined temperature;
   removing said cast and thermoformable tubular liner from said oven and allowing said cast and thermoformable tubular liner to cool to room temperature; and
   removing said thermoformable tubular liner from said cast;
   whereby an interior surface of said thermoformable tubular liner conforms to the shape of said positive cast.

12. A method of making a thermoformable tubular liner for use in a prosthetic appliance, comprising the steps of:
   preparing a negative cast from a patient's residual limb;
   preparing a positive cast from said negative cast;
   placing a thermoformable tubular liner over said positive cast;
   formulating said thermoformable tubular liner so that it has elastomeric qualities and exhibits a durometer of 40 to 60 on the "00" scale;
   heating said positive cast and thermoformable tubular liner in an oven for a predetermined amount of time at a predetermined temperature;
   removing said cast and thermoformable tubular liner from said oven and allowing said cast and thermoformable tubular liner to cool to room temperature; and
   removing said thermoformable tubular liner from said cast;
   whereby an interior surface of said thermoformable tubular liner conforms to the shape of said positive cast.

13. A method of making a thermoformable tubular liner for use in a prosthetic appliance, comprising the steps of:
   preparing a negative cast from a patient's residual limb;
   preparing a positive cast from said negative cast;

heating a thermoformable tubular liner in an oven for a predetermined amount of time at a predetermined temperature so that said thermoformable tubular liner becomes pliable and acquires a new geometry;

removing said thermoformable tubular liner from said oven and placing said thermoformable tubular liner over said positive cast and allowing said thermoformable tubular liner to cool to room temperature;

removing said thermoformable tubular liner from said positive cast;

an interior surface of said thermoformable tubular liner conforming to the shape of said positive cast;

said thermoformable tubular liner exhibiting elasticity when cooled to room temperature and returning to its new geometry when stretched and released at room temperature;

said thermoformable tubular liner adapted to be stretched and fitted over a residual limb;

whereby said thermoformable tubular liner remains on said residual limb even as said residual limb shrinks during the day.

14. The method of claim 13, wherein said predetermined amount of time is about thirty minutes.

15. The method of claim 14, wherein said predetermined temperature is about ninety to one hundred degrees Celsius.

16. The method of claim 13, further comprising the step of preheating said positive cast in said oven for a predetermined amount of time at a predetermined temperature prior to said step of placing said thermoformable tubular liner over said positive cast.

17. The method of claim 16, wherein said predetermined amount of time of said preheating step is about two to three hours.

18. The method of claim 16, wherein said predetermined temperature of said preheating step is about ninety to one hundred degrees Celsius.

19. The method of claim 13, further comprising the step of formulating said thermoformable tubular liner by mixing triblock copolymers of the styrene, ethylene styrene type with mineral oils at a predetermined concentration.

20. The method of claim 19, wherein said predetermined concentration is about 200 to 400 parts of mineral oil per 100 parts of polymer.

21. The method of claim 13, further comprising the step of applying a fabric in overlying relation to an exterior surface of said liner.

22. The method of claim 21, wherein the step of applying the fabric is performed after the step of placing the thermoformable tubular liner over the positive cast and prior to the step of heating the positive cast and thermoformable tubular liner in the oven.

23. A method of making a thermoformable tubular liner for use in a prosthetic appliance, comprising the steps of:

preparing a negative cast from a patient's residual limb;

preparing a positive cast from said negative cast;

formulating a thermoformable tubular liner by mixing triblock copolymers of the styrene, ethylene styrene type with mineral oils at a predetermined concentration;

heating said thermoformable tubular liner in an oven for a predetermined amount of time at a predetermined temperature;

removing said thermoformable tubular liner from said oven and placing said thermoformable tubular liner over said positive cast and allowing said cast and thermoformable liner to cool to room temperature; and removing said thermoformable tubular liner from said cast, whereby an interior surface of said thermoformable tubular liner conforms to the shape of said positive cast.

24. A method of making a thermoformable tubular liner for use in a prosthetic appliance, comprising the steps of:

preparing a negative cast from a patient's residual limb;

preparing a positive cast from said negative cast;

formulating a thermoformable tubular liner so that it has elastomeric qualities and exhibits a durometer of 40 to 60 on the "00" scale;

heating said thermoformable tubular liner in an oven for a predetermined amount of time at a predetermined temperature;

removing said thermoformable tubular liner from said oven and placing said thermoformable tubular liner over said positive cast and allowing said cast and thermoformable tubular liner to cool to room temperature; and removing said thermoformable tubular liner from said positive cast;

whereby an interior surface of said thermoformable tubular liner conforms to the shape of said positive cast.

* * * * *